United States Patent [19]
Bakaysa et al.

[11] Patent Number: 5,474,978
[45] Date of Patent: Dec. 12, 1995

[54] INSULIN ANALOG FORMULATIONS

[75] Inventors: Diane L. Bakaysa; David N. Brems; Bruce H. Frank; Henry A. Havel; Allen H. Pekar, all of Indianapolis, Ind.

[73] Assignee: Eli Lilly and Company, Indianapolis, Ind.

[21] Appl. No.: 260,634

[22] Filed: Jun. 16, 1994

[51] Int. Cl.$^6$ .............................. A61K 38/28; C07K 14/62
[52] U.S. Cl. .................................... 514/4; 514/3; 530/304
[58] Field of Search ................................ 530/304; 514/3, 514/4

[56] References Cited

U.S. PATENT DOCUMENTS

| | | | |
|---|---|---|---|
| 3,060,093 | 10/1962 | Poulsen et al. | 167/75 |
| 4,608,634 | 6/1986 | Grau | 514/4 |
| 5,028,587 | 7/1991 | Dörschug et al. | 514/3 |
| 5,149,777 | 9/1992 | Hansen et al. | 530/303 |
| 5,164,366 | 11/1992 | Balschmidt et al. | 514/3 |

FOREIGN PATENT DOCUMENTS

| | | |
|---|---|---|
| 0214826 | 3/1987 | European Pat. Off. . |
| 0375437 | 6/1990 | European Pat. Off. . |
| 0383472 | 8/1990 | European Pat. Off. . |
| WO90/07522 | 7/1990 | WIPO . |
| WO95/00550 | 1/1995 | WIPO ............................... C07K 7/40 |

OTHER PUBLICATIONS

Ser. No. 08/057201, Chance, et al. May 5, 1993.
Howey, et al., *Diabetes*, 43, 396–402 (Mar. 1994).
*Diabetes*, 41, Suppl. 1, 192A (1992).
Brems, et al., *Protein Engineering*, 5:6, 519–525 (1992).
Heinemann, et al., *Diabetologia*, 33, 384–386 (1990).
Kirk–Othmer, *Encyclopedia of Chemical Technology 13*, 607–614 (1981).
Bruce H. Frank, Text and Slide copies of lecture given at the Conference on Insulin, Self Association and Conformational Studies on Human Proinsulin and Insulin Analogs, University of York, Aug. 29–Sep. 1, 1989.
Wollmer et al., *Phenol–Promoted Structural Transformation of Insulin in Solution* from the 2nd Assisi International Symposium on Advanced Models for the Therapy of Insulin–Dependent Diabetes, 903–911 (Apr. 1986).
*Diabetologia*, 30, 503A, (1987).
Brange, et al., *Nature*, 333:16, 679–682 (Jun. 1988).
Brange, et al., *Diabetes Care*, 13:9, 923–954 (Sep. 1990).
Dodson, et al., *Phil Trans. R. Soc. Lond. A* 345, 153–164 (1993).
Brange, *Galenics of Insulin: The Physico–chemical and Pharmaceutical Aspects of Insulin and Insulin Preparations*, Springer–Verlag Berlin Heidelberg, Germany (1987) pp. 1–103.
Wollmer, et al., *Biol. Chem. Hoppe–Seyler*, 370, 1045–1053 (Sep. 1989).
Brems, et al., *Protein Engineering*, 5:6, 527–533 (1992).
Derewenda, et al., *Nature*, 338:13, 594–596 (Apr. 1989).
Brader, et al., *Biochemistry*, 30, 6636–6645 (1991).
Harding, et al., *The Crystal Structure of Insulin: II. An Investigation of Rhombohedral Zinc Insulin Crystals and a Report of Other Crystalline Forms* Chemical Crystallography Laboratory, South Parks Road, Oxford, England, 212–226 (8 Nov. 1965).
Brange, et al., *Structural Biology*, 1, 934–940 (1991).

*Primary Examiner*—Jill Warden
*Assistant Examiner*—Benet Prickril
*Attorney, Agent, or Firm*—Steven P. Caltrider; David E. Boone; Gerald V. Dahling

[57] ABSTRACT

The present invention discloses a human insulin analog hexamer complex and formulations. More specifically, the present invention relates to various parenteral formulations, which comprise: human insulin analogs in a hexamer conformation, zinc ions, and at least three molecules of a phenolic derivative selected from the group consisting of m-cresol, phenol, or a mixture of m-cresol and phenol. The formulation provides a rapid onset of action.

13 Claims, 3 Drawing Sheets

INSULIN ANALOG FORMULATIONS

FIELD OF THE INVENTION

The present invention relates to monomeric analogs of human insulin. More specifically, the present invention relates to a hexamer complex comprising an insulin analog, zinc, and a phenolic derivative.

BACKGROUND OF THE INVENTION

Since the introduction of insulin in the 1920's, continuous strides have been made to improve the treatment of diabetes mellitus. Major advances have been made in insulin. purity, and availability. Various formulations with different timeactions have also been developed. Despite these improvements, subcutaneous injection therapy still falls short of providing the patient with convenient regulation and normalized glycemic control. Frequent excursions from normal glycemia levels over a patient's lifetime lead to hyper-or hypoglycemia, and long term complications including retinopathy, neuropathy, nephropathy, and micro- and macroangiopathy.

To help avoid extreme glycemic levels, diabetics often practice multiple injection therapy whereby insulin is administered with each meal. However, this therapy has not yet been optimized. The most rapid-acting insulin commercially available peaks too late after injection and lasts too long to optimally control glucose levels. Recently, considerable effort has been devoted to create insulin formulations and insulin analog formulations that alter the kinetics of the subcutaneous absorption process.

Because all commercial pharmaceutical formulations of insulin contain insulin in the self-associated state and predominately in the zinc-hexamer form, it is believed that the rate-limiting step for the absorption of insulin from the subcutaneous injection depot to the bloodstream is the dissociation of the self-aggregated insulin hexamer. Brange et al. in *Diabetes Care* 13: 923–954 (1990). To accelerate this absorption process, monomeric insulin analogs have been developed. These monomeric analogs possess a comparatively more rapid onset of activity than insulin while retaining the biological activity of native human insulin. They provide a rapid absorption to bring the injection time and peak action of insulin into closer proximity with postprandial glucose excursion associated in the response to a meal. The preparation of various monomeric analogs is disclosed in U.S. patent application Ser. No. 07/388,201 (Chance et al., EPO publication number 383 472), and Brange et al., EPO publication number 214 826.

unfortunately, the modifications to insulin, which cause these analogs to be monomeric, also result in a high rate of polymer formation in parenteral formulations. Because the expiration of insulin preparations occurs when levels of 1% polymer are obtained (U.S. Pharmacopoeia, 1990), minimizing this type of degradation is extremely important in reducing undesirable side effects. Therefore, it was desirable to formulate monomeric analogs in such a manner to cause the analog to self-associate to form a stable conformation, yet maintain its rapid absorption.

The addition of certain metal ions, primarily zinc, enhance the chemical stability by driving the insulin to associate and form hexamers, specifically the $Zn(II)$-$T_6$ conformation. Further, phenolics have been shown to specifically bind to the insulin hexamer and induce an allosteric conformational change whereby the eight N-terminal amino acids of the B-chain are converted from the extended conformation to an alpha-helix. Derewenda, et al. *Nature*, 338: 594–596 (1989). This phenolic-bound conformation state is known as the $Zn(II)$-R state.

In stark contrast to these well-established observations that insulin readily aggregates in the presence of zinc to form well defined, stable zn-hexamer structure, early studies with monomeric insulin analogs revealed that any aggregation between zinc and the insulin analog is distinct from that observed with insulin. B. H. Frank, Text and Slide copies of Lecture given at the Conference on Insulin "Self-Association and Conformational Studies on Human Proinsulin and Insulin Analogs", University of York, (Aug. 29–Sep. 1, 1989). Further, the highly stable Zn-hexamer complex as seen with insulin is not observed with monomeric analogs. Id. Brems et al. *Protein Engineering*, 5:6, 527–533 (1992), disclose that monomeric $Lys^{B28}Pro^{B29}$-hI is less prone to dimerization and self-association to higher molecular weight forms than human insulin. Brems et al. continue to conclude that $Asp^{B28}Pro^{B29}$-hI, $Ala^{B28}Pro^{B29}$-hI, and $Lys^{B28}Pro^{B29}$-hI show little or no Zn-induced association and that $Pro^{B29}$ insulin, $Lys^{B28}$ insulin, $Asp^{B28}$ insulin, and $Ala^{B28}$ insulin demonstrate Zn-induced association, but less than Zn-insulin. Subsequent, unpublished experimental observations by the present inventors suggest that association with zinc is observed; however, such association between the analog and zinc differs from insulin. The association that is observed with these analogs is to a multitude of higher molecular weight forms and distinct from the predominate, welldefined, Zn-insulin hexamers. Therefore, it is clear that monomeric insulin analogs do not form the $Zn(II)$-$T_6$ conformation in a manner analogous to insulin.

In view of the published literature, it is surprising that the present invention affords monomeric insulin analogs in a well defined, stable zinc-phenol hexamer complex. This hexamer complex is uniquely different from those complexes observed with insulin under identical conditions. Insulin complexes with zinc and phenol are in a $Zn(II)$-$R_6$ conformation. The hexamer complex of the present invention is not identical to this conformation. Also quite remarkably, the insulin analog hexamer complex has a much greater propensity to dissociate than insulin. This propensity to dissociate translates into the desired fast-acting property.

Brange et al. in *Current Opinion in Structural Biology* 1:934–940 (1991) disclose various fast-acting stable insulin monomers and state that the obvious route to creating a fast-acting insulin is to prevent dimer or hexamer formation. Likewise, Brange et al. in *Diabetes Care* 13: 923–954 (1990) disclose that when insulin is administered as a hexamer, in addition to its slower free diffusion, the hexamer must be sterically more hindered than a monomer during the diffusion transport in the subcutis and/or during its passage through the capillary membrane. Further when injected subcutaneously, the $Zn(II)$-$R_6$ conformation does not dissociate directly but must transform through the $Zn(II)$-$T_6$ conformation. These conformational changes and the dissociation therefrom delay the onset of activity. Therefore, one skilled in the art at the time of invention believed that efforts to chemically stabilize the monomeric insulin analog with zinc by forming a well defined, hexamer complex would be unsuccessful, or if successful, would sacrifice the rapid onset of action desired.

The present formulation is a zinc-phenolic induced hexamer complex that is absorbed rapidly. The rate of absorption for the hexamer complex is at least two times that observed with insulin. Yet, when the hexamer complex is formulated, it is equally stable when compared to insulin against chemical degradation. Therefore, it is surprising that the present invention converts a monomeric insulin analog to a well-defined, stable zinc-phenol hexamer complex. Remarkably; when formulated, this hexamer complex retains the fast-acting properties associated with the monomeric insulin analog. Accordingly, the present invention provides a parenteral formulations of the insulin analog hexamer complex that is stable and fast-acting.

SUMMARY OF THE INVENTION

This invention provides a human insulin analog complex, which comprises: six molecules of a human insulin analog, two zinc ions, and at lease three molecules of a phenolic derivative selected from the group consisting of m-cresol, phenol, or a mixture of m-cresol and phenol; such that the analog complex is a hexamer. The invention further provides parenteral formulations comprising the hexamer complex.

DETAILED DESCRIPTION AND PREFERRED EMBODIMENTS

Figure 1:
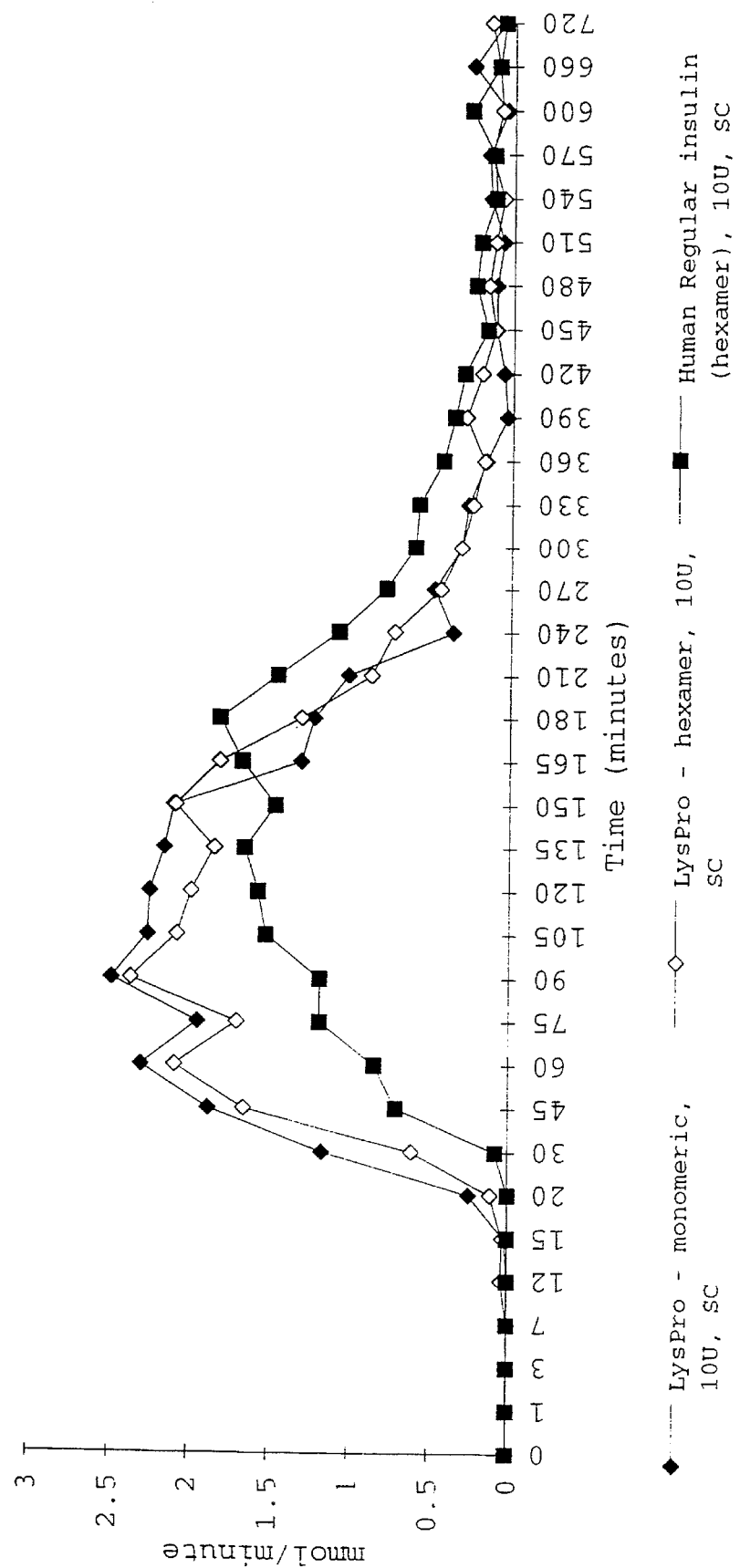
FIG. 1 is a graphical representation of the profile of action of $Lys^{B28}Pro^{B29}$-hI and human insulin. The graph is the mean glucose infusion response rate. The figure demonstrates the advantages of the present invention.

As noted above, the invention provides a monomeric human insulin analog complex as a hexamer. The term "monomeric insulin analog" or "human insulin analog" as used herein is human insulin wherein:

Pro at postion B28 is substituted with Asp, Lys, Leu, Val, or Ala; and Lys at position B29 is Lysine or substituted with Proline;

des(B28-B30); or des(B27). Monomeric insulin analogs are described in Chance et al., U.S. patent application Ser. No. 07/388,201, (EPO publication number 383 472), and Brange et al., EPO publication 214 826, and are herein incorporated by reference. Monomeric insulin analogs are less prone to dimerization or self-association than insulin.

One skilled in the art would recognize that other modifications are possible. These modifications are widely accepted in the are and include replacement of the histidine residue at position B10 with aspartic acid; replacement of the phenylalanine residue at position B1 with aspartic acid; replacement of the threonine residue at position B30 with alanine; replacement of the serine residue at position B9 with aspartic acid; deletion of amino acids at position B1 alone or in combination with a deletion at position B2; and deletion of threonine from position B30.

All amino acid abbreviations used in this disclosure are those accepted by the United States Patent & Trademark Office as set forth in 37 C.F.R. § 1.822(b)(2). A particularly preferred monomeric insulin analog is $Lys^{B28}Pro^{B29}$-human insulin (B28 is Lys; B29 is Pro).

The term "treating", as used herein, describes the management and care of a patient for the purpose of combating the disease, condition, or disorder and includes the administration of a compound of present invention to prevent the onset of the symptoms or complications, alleviating the symptoms or complications, or eliminating the disease, condition, or disorder.

The term "isotonicity agent" refers to an agent that is physiologically tolerated and embarks a suitable tonicity to the formulation to prevent the net flow of water across the cell membrane. Compounds, such as glycerin, are commonly used for such purposes at known concentrations.

The term "phenolic derivative" or "phenolic" is m-cresol, phenol or a mixture of m-cresol and phenol. Preferably, phenolic is m-cresol.

The term "physiologically tolerated buffer" is known in the art. A physiologically tolerated buffer is preferably a phosphate buffer, like sodium phosphate. Other physiologically tolerated buffers include TRIS, sodium acetate, or sodium citrate. The selection and concentration of buffer is known in the art.

The insulin analogs of the present invention complex with zinc ions and a phenolic derivative to form a stable, hexamer conformation. Both the zinc and phenolic derivative are critical to achieve a complex that is stable and capable of rapid dissociation and onset of action. The hexamer complex consists of two zinc ions per hexamer of human insulin analog and at least three molecules of a phenolic derivative selected from the group consisting of m-cresol, phenol, or a mixture of m-cresol and phenol.

Soluble monomeric analog is converted to the hexamer complex by dissolving the monomeric analog in a diluent containing the phenolic derivative at a pH of about 7.5 and adding zinc. Zinc is preferably added as a salt. Representative examples of zinc salts include zinc acetate, zinc bromide, zinc chloride, zinc fluoride, zinc iodide and zinc sulfate. The skilled artisan will recognize that there are many other zinc salts which also might be used in the process of the present invention. Preferably, zinc acetate or zinc chloride is used because these salts do not add new chemical ions to commercially accepted processes.

Dissolution of the analog may be aided by what is commonly known as an acid dissolution, i.e., the pH is lowered to about 3.0 to 3.5 with a physiologically tolerated acid, preferably HCl to aid in the dissolution of the monomeric analog. Other physiologically tolerated acids include acetic acid, citric acid, and phosphoric acid. The pH is then adjusted with a physiologically tolerated base, preferably sodium hydroxide to about 7.4 to 7.5. Other physiologically tolerated bases include potassium hydroxide and ammonium hydroxide.

The hexamer complex may be formulated into stable, rapid acting parenteral formulations. The concentration of insulin analog in the formulation is about 0.5 mg/ml to about 20 mg/ml; preferably about 1.2 mg/ml to about 17.5 mg/ml; most preferably, about 3.5 mg/ml. In general, the concentration of zinc is about 10 µg/ml to about 50 µg/ml. The optimal concentration of zinc in the formulation is from about 14 µg/ml to about 35 µg/ml, of which two zinc ions are bound to each hexamer. When formulated, the hexamer complex binds as many as seven phenolics. Generally, when formulated six phenolics are bound to the hexamer. Accordingly, excess phenolic is preferably added to the formulation. The phenolic also acts as a preservative. Therefore, the preferred concentration is about 23 mM to 35 mM, most preferably 29 mM. The phenolic is preferably m-cresol.

An isotonicity agent, preferably glycerin, may be added to the formulation. The concentration of the isotonicity agent is in the range known in the art for insulin formulations, preferably about 16 mg/ml. The pH of the formulation may be buffered with a physiologically tolerated buffer, preferably a phosphate buffer, like sodium phosphate.

At the time of invention, the published literature suggested that one skilled in the art needed to eliminate aggregation in order to get rapid absorption. Therefore, it is quite surprising that the formulated hexamer analog brings a rapid onset of action. Unlike insulin, the formation of an insulin analog hexamer complex does not adversely effect the time required to achieve peak serum insulin analog concentration. FIG. 1 demonstrates, in human patients, the mean glucose infusion rate response to a formulation containing monomeric $Lys^{B28}Pro^{B29}$-hI (formulated without zinc); a formulated $Lys^{B28}Pro^{B29}$-hI hexamer; and human Regular insulin. The formulated hexamer complex retains the rapid action of monomeric $Lys^{B28}Pro^{B29}$-hI. The absorption rate is significantly more rapid than Regular human insulin. Thus, the results in FIG. 1 illustrate: First, hexamer $Lys^{B28}Pro^{B29}$-hI and monomeric $Lys^{B28}Pro^{B29}$-hI have similar rates of absorption; second, both hexameric and monomeric $Lys^{B28}Pro^{B29}$-hI have faster rates of absorption than insulin.

The formulation comprising the insulin analog complex as hexamer is stable. In comparative studies, monomeric $Lys^{B28}Pro^{B29}$-hI shows the greatest rate of degradation with a 1.63% per week increase in polymer formation over the six week study. Unformulated human insulin undergoes a slower rate of polymer formation of 0.61% per week. Upon formulation, however, the rate of high molecular weight polymer formation is reduced to 0.095% per week for insulin. Formulated $Lys^{B28}Pro^{B29}$-hI, as a hexamer complex, exhibits a diminished rate of higher molecular weight polymer formation of 0.11% per week, which is comparable to the rate seen for formulated insulin. These studies are exemplified in Example 1 and illustrated in FIG. 2.

The insulin analog of the present invention can be prepared by any of a variety of recognized peptide synthesis techniques including classical (solution) methods, solid phase methods, semi synthetic methods, and more recent recombinant DNA methods. For example, Chance et al., U.S. patent application Ser. No. 07/388,201, EPO publication number 383 472, and Brange et al., EPO publication number 214 826, disclose the preparation of various monomeric analogs.

The following examples and preparations are provided merely to further illustrate the preparation of the insulin analogs and the invention. The scope of the invention is not construed as merely consisting of the following examples.

Preparation 1

Protein stock Preparation

Unformulated samples of insulin and $Lys^{B28}Pro^{B29}$-hI were prepared at 3.5 mg/ml in 7 mM sodium phosphate, and with or without 1.25 mg/ml m-cresol, 1.09 mg/ml phenol and 16 mg/ml glycerol, depending on the experiment performed. Samples of $Lys^{B28}Pro^{B29}$-hI as a hexamer complex were prepared in an identical fashion except 19.7 μg/ml zinc was added. All samples were taken through an acid excursion step to pH 3.0 at which time zinc was added in the formulation lots. The pH was then adjusted to 7.4. Protein concentrations were determined prior to the addition of phenolics by UV absorption spectroscopy using an AVIV model 14 DS double-beam spectrophotometer. Protein concentrations were calculated as described in Frank, B. H., Pekar, A. H. and Veros, A. J. (1972) *Diabetes,* 21 (suppl. 2), 486–491.

Example 1

Chemical Stability

Figure 2:
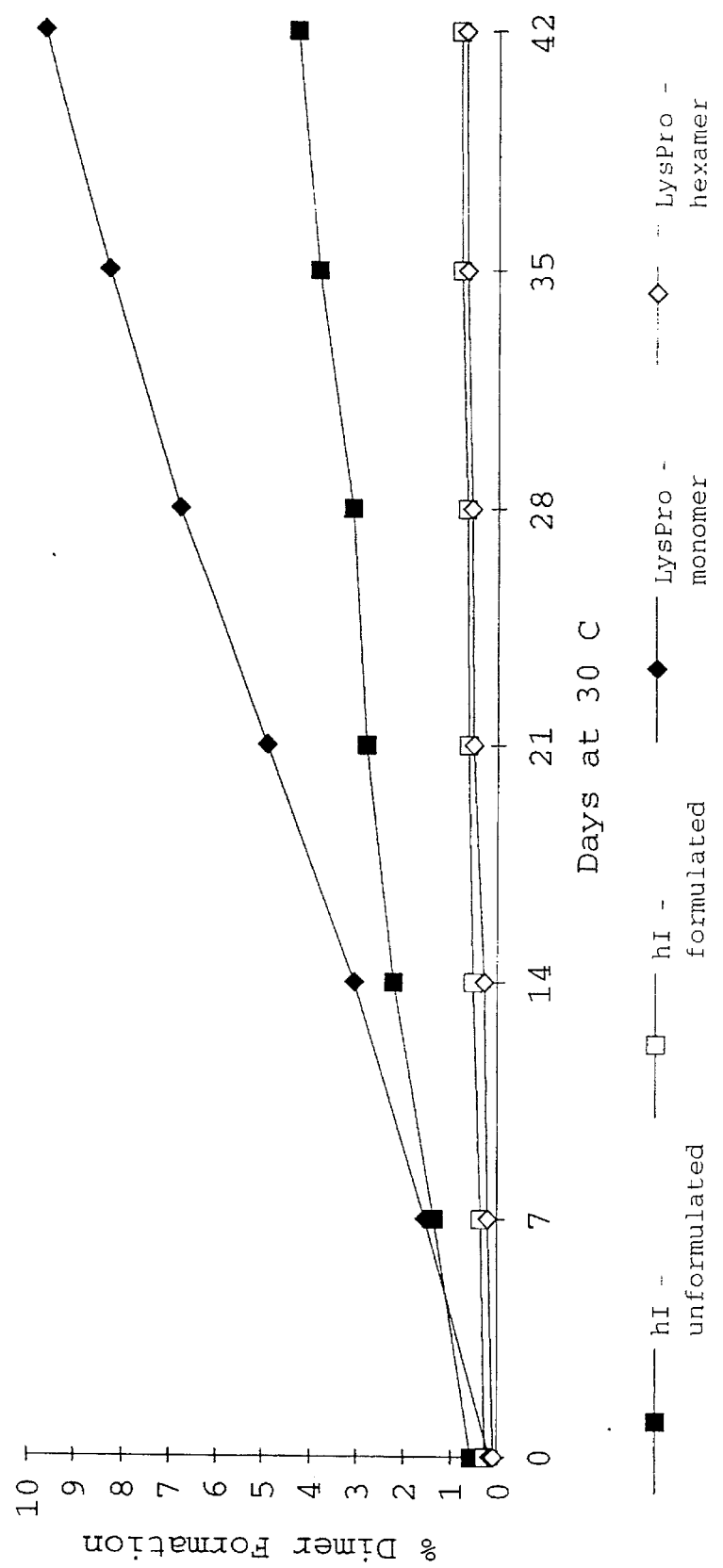
FIG. 2 is a graphical representation of the stability of $Lys^{B28}Pro^{B29}$-human insulin. The graph represents stability by measuring the polymer formation of the insulin analog in the hexamer association compared to monomeric $Lys^{B28}pro^{B29}$-human insulin and insulin. The figure demonstrates the advantages of the present invention.

Degradation is initiated by incubating formulated and unformulated preparations of insulin and monomeric and hexameric $Lys^{B28}Pro^{B29}$-hI at 30° C. The formulated insulin and hexamer $Lys^{B28}Pro^{B29}$-hI contained: 3.5 mg/ml protein, 16 mg/ml glycerol, 7 mM dibasic sodium phosphate heptahydrate, 1.25 mg/ml m-cresol, 1.09 mg/ml phenol, and 0.0245 mg/ml zinc oxide at a pH of 7.3 to 7.4. The unformulated insulin and monomeric $Lys^{B28}Pro^{B29}$-hI contained: 3.5 mg/ml protein, 16 mg/ml glycerol, 7 mM dibasic sodium phosphate heptahydrate, 1.25 mg/ml m-cresol, and 1.09 mg/ml phenol at a pH of 7.3 to 7.4. At seven day intervals, samples were removed from the 30° C. incubation and assayed for formation of high molecular weight species using size-exclusion HPLC. Analysis is performed by injecting 20 μl samples into a Dupont Zorbax GF-250 Special (9.4×250 mm) column using a mixture of 0.4M ammonium bicarbonate and acetonitrile as the eluting solution (flow rate of 0.5 ml/min at ambient temperature and detection at 214 nm). The percent polymer formation is determined from the ratio of the high molecular weight peak to the total area of the monomer and high molecular weight peaks. The results are illustrated in FIG. 2.

Example 2

Static Light Scattering

The in vitro dissociation properties of monomeric $Lys^{B28}Pro^{B29}$-hI, $Lys^{B28}Pro^{B29}$-hI as a hexamer complex, and insulin are probed using static light scattering.

Three formulated and unformulated protein stock solutions are prepared as described except that the unformulated protein stock solutions did not contain zinc, glycerol, or preservatives. Using these 3.5 mg/ml stocks, a series of dilutions is prepared for both insulin and $Lys^{B28}Pro^{B29}$-hI spanning the protein concentration range of 3.5 mg/ml to 0.2 mg/ml. All dilutions are made to a final volume of 10 ml with 7 mM sodium phosphate buffer, pH 7.4, in order to mimic the subcutaneous site upon injection. All solutions were filtered through 0.2 μm Gelman low protein binding filters before performing SLS measurements. The protein concentration for these samples is determined using reversed phase HPLC.

For analysis of the formulated samples, protein-free solvent blanks were prepared for each set of protein samples. These blanks contained excipients at the same concentration as the corresponding protein sample sets. For analysis of the unformulated samples, a single blank of 7 mM sodium phosphate is used. Using these appropriate solvent blanks insured that data reflected only solute scatter and not an added contribution due to solvent changes.

Static light scattering (SLS) experiments are performed using a Brookhaven Instruments 2030AT autocorrelator and goniometer. All measurements are made with a 1 mm pinhole at 90° scattering angle using a Lexel Model 3500 argon ion laser set at 488 nm. The temperature is maintained at 25° C. by a Neslab RTE-110 temperature bath. The signal at the photomultiplier tube is calibrated using 0.1 μm filtered toluene.

Figure 3:
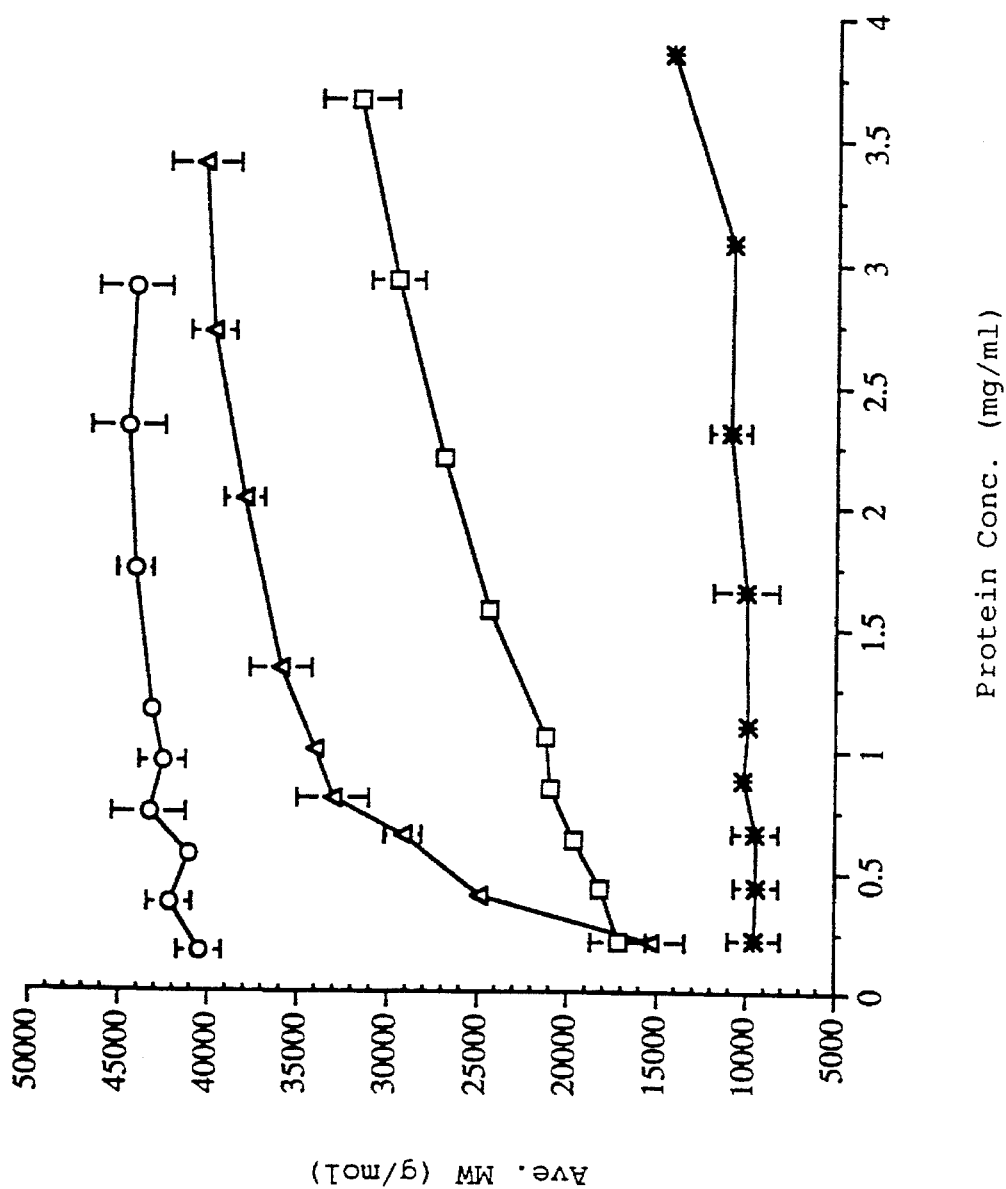
FIG. 3 is a graphical representation of the dissociation of $Lys^{B28}Pro^{B29}$-human insulin in a hexamer complex. The graph is the in vitro dissociation of formulated insulin (o); $Lys^{B28}Pro^{B29}$-hI formulated as a hexamer complex ($\Delta$); unformulated insulin ($\square$); and monomeric $Lys^{B28}Pro^{B29}$-hI (*) monitored by static light scattering at 488 nm at a 90° angle. The formulated samples contained 0.5 mol Zn per mol protein, 1.25 mg/ml m-cresol and 1.09 mg/ml phenol, 7 mM sodium phosphate and 16 mg/ml glycerol. The unformulated and monomeric samples contained no additional excipients. The figure demonstrates the advantages of the present invention.

Weight-average molecular weights are calculated using the equations described in Cantor, C. R., and Schimmel, P. R., *Biophysical Chemistry*, W. H. Freeman and Company, New York, pp. 838–843 (1982). FIG. 3 discloses the results of the light scattering study. The in vitro dissociation profile of $Lys^{B28}Pro^{B29}$-hI as a hexamer complex and insulin are quite different. The insulin analog results demonstrate a rapid dissociation, which allows for a faster absorption than human insulin. Even though both preparations contain hexameric association states and the formulations are equally stable against chemical degradation, hexamer $Lys^{B28}Pro^{B29}$-hI has a greater propensity to dissociate than insulin.

We claim:

1. A human insulin analog complex, which comprises: six molecules of a human insulin analog, two zinc ions, and at least three molecules of a phenolic derivative selected from the group consisting of m-cresol, phenol, or a mixture of m-cresol and phenol; such that the insulin analog complex is a hexamer; wherein the human insulin analog is human insulin wherein Pro at position B28 is substituted with Asp, Lys, Leu, Val, or Ala, and Lys at position B29 is Lys or Pro; des(B28-B30)-human insulin; or des (B27)-human insulin.

2. A parenteral pharmaceutical formulation comprising the human insulin analog complex of claim 1.

3. The parenteral pharmaceutical formulation of claim 2, which further comprises an isotonicity agent.

4. The parenteral pharmaceutical formulation of claim 3, which further comprises a physiologically tolerated buffer.

5. The parenteral pharmaceutical formulation of claim 4, wherein the buffer is sodium phosphate.

6. The parenteral pharmaceutical formulation of claim 5, wherein the isotonicity agent is glycerol.

7. The parenteral pharmaceutical formulation of claim 6, wherein the phenolic derivative is m-cresol.

8. The parenteral pharmaceutical formulation of claim 7, wherein the human insulin analog is $Lys^{B28}Pro^{B29}$-human insulin.

9. A human insulin analog composition of claim 1, wherein the human insulin analog is $Lys^{B28}Pro^{B29}$-human insulin.

10. A method of treating a patient suffering from diabetes mellitus, which comprises administering to said patient a pharmaceutical formulation containing the composition of claim 1.

11. The method of claim 10, wherein the human insulin analog is $Lys^{B28}Pro^{B29}$-human insulin.

12. A human insulin analog complex, consisting of: six molecules of a human insulin analog, two zinc ions, and at least three molecules of a phenolic derivative selected from the group consisting of m-cresol, phenol, or a mixture of m-cresol and phenol; such that the insulin analog complex is a hexamer;

wherein the human insulin analog is human insulin wherein Pro at position B28 is substituted with Asp, Lye, Leu, Val, or Ala, and Lys at position B29 is Lys or Pro; des(B28-B30)-human insulin; or des(B27)-human insulin.

13. A parenteral pharmaceutical formulation consisting of: about 3.5 mg/mL $Lys^{B28}Pro^{B29}$-human insulin, about 19.7 μg/mL zinc, about 7 mM sodium phosphate, about 16 mg/mL glycerin, and about 29 mM m-cresol; wherein $Lys^{B28}Pro^{B29}$-human insulin is a hexamer.

* * * * *

UNITED STATES PATENT AND TRADEMARK OFFICE
CERTIFICATE OF CORRECTION

PATENT NO. : 5,474,978
DATED : December 12, 1995
INVENTOR(S) : Diane L. Bakaysa, et al It is certified that error appears in the above-indentified patent and that said Letters Patent is hereby corrected as shown below:

Column 1, Line 13   remove the period after "insulin"

Column 3, Line 13   "lease" should appear as "least"

Column 3, Line 63   "are" should appear as "art"

Column 8, Line 27   "Lye" should appear as "Lys"

Signed and Sealed this

Fourth Day of March, 1997

Attest:

BRUCE LEHMAN

Attesting Officer

Commissioner of Patents and Trademarks